United States Patent
Stratton

(10) Patent No.: US 6,228,101 B1
(45) Date of Patent: May 8, 2001

(54) BREATHING ASSISTANCE IMPROVEMENTS

(75) Inventor: Barrie Raymond Stratton, Bridgwater (AU)

(73) Assignee: BRS Enterprises Pty. Ltd., Kent Town (AU)

(*) Notice: Subject to any disclaimer, the term of this patent is extended or adjusted under 35 U.S.C. 154(b) by 0 days.

(21) Appl. No.: 09/155,793

(22) PCT Filed: Sep. 25, 1997

(86) PCT No.: PCT/AU97/00634

§ 371 Date: Oct. 5, 1998

§ 102(e) Date: Oct. 5, 1998

(87) PCT Pub. No.: WO98/12998

PCT Pub. Date: Apr. 2, 1998

(30) Foreign Application Priority Data

Sep. 27, 1996 (AU) .................................. 65890/96

(51) Int. Cl.[7] .................................................. A61M 29/00
(52) U.S. Cl. ...................................... 606/199; 128/200.24
(58) Field of Search ........................... 606/199, 204.15, 606/204.45; 128/898, 200.24, 204.12

(56) References Cited

U.S. PATENT DOCUMENTS

| 5,546,929 | 8/1996 | Muchin | 128/200.24 |
| 5,549,103 | 8/1996 | Johnson | 128/200.24 |
| 5,553,605 | 9/1996 | Muchin | 128/200.24 |
| 5,669,377 | * 9/1997 | Fenn | 606/199 |
| 5,769,089 | * 6/1998 | Hand et al. | 606/199 |
| 5,913,873 | * 6/1999 | Blach et al. | 606/199 |
| 5,931,854 | * 8/1999 | Dillon | 606/199 |
| 5,961,537 | * 10/1999 | Gould | 606/204.45 |

FOREIGN PATENT DOCUMENTS

WO94/23675  10/1994 (WO) .............................. A61F/5/56

* cited by examiner

*Primary Examiner*—Glenn K. Dawson
(74) *Attorney, Agent, or Firm*—Baker & Maxham

(57) ABSTRACT

Assistance for breathing is provided for both humans and animals by providing for a member to adhere along only one or separately both sides of a nose and having a shape so that a part of the member can adhere over a bone of the nose and then in cantilever fashion adhere to and thereby support soft flesh forming an outer side of a nasal passage so as to keep this open even with heavy breathing.

1 Claim, 2 Drawing Sheets

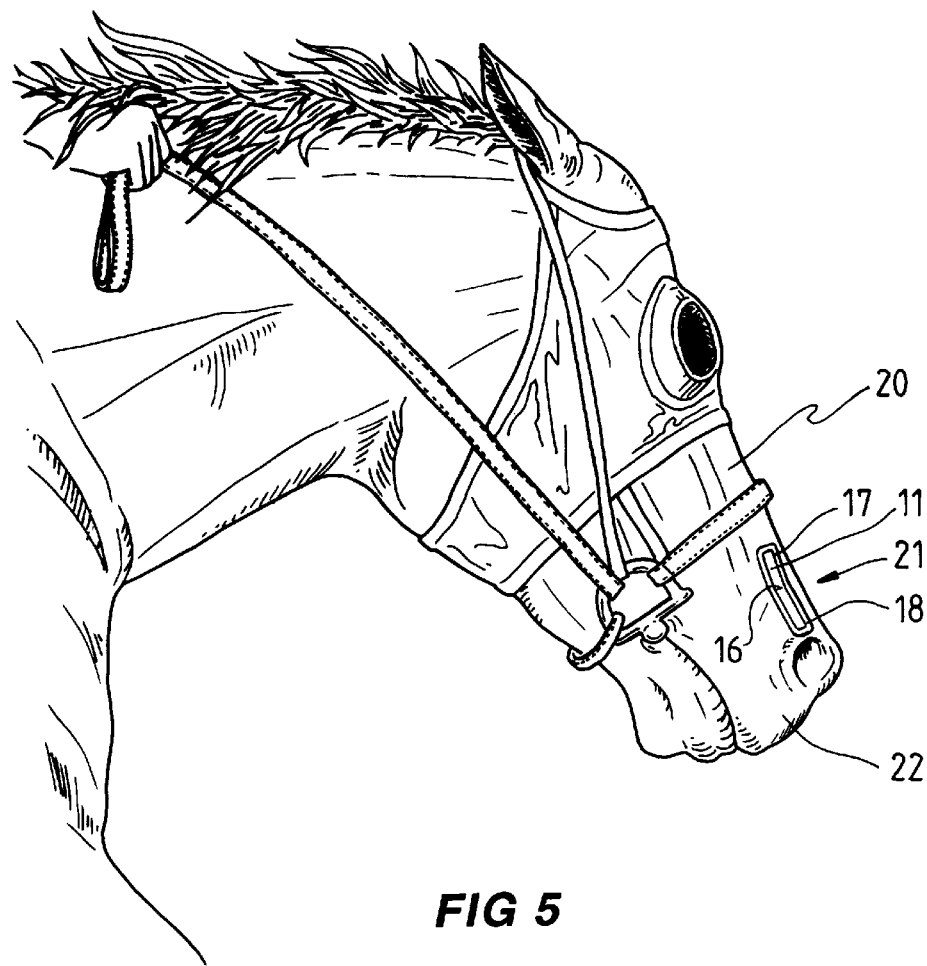
FIG 5
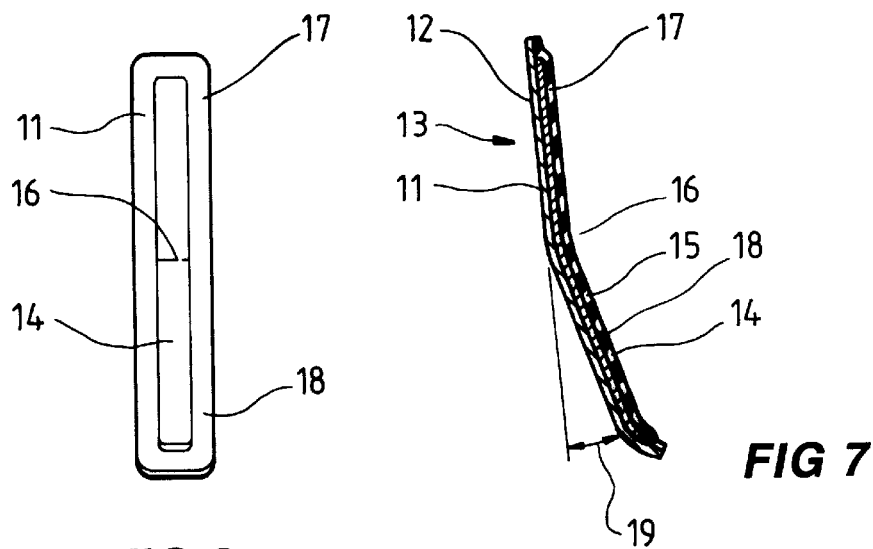
FIG 6  FIG 7

BREATHING ASSISTANCE IMPROVEMENTS

BACKGROUND OF THE INVENTION

1. Field of the Invention

This invention relates to a method and means to assist breathing for both humans and some animals.

2. Discussion of Prior Art

The problem to which this invention is directed is the same problem as that set out in U.S. Pat. No. 5,533,499 which is directed to a nasal dilator which assists in resisting the drawing together of outer wall tissue of the nasal passage during breathing.

It is known that air passing through a nasal passage will, especially where that passage is other than circular, cause a drawing together of the closer walls through a bernoulli effect. This implicitly causes a further narrowing of the passageway. This effect is known to occur with many people. The result is that they may suffer sufficiently substantial restriction in passage cross sectional area that they can be forced to breathe additionally through their mouth or suffer effects such as snoring and even sleep apnoea. In other cases athletes can have their breathing restricted by this effect so limiting their performance.

U.S. Pat. No. 5,533,499 proposes a flexible strip which traverses from one side of the nose across the bridge of the nose to the other side and so that one end adheres to the skin adjacent one nasal passage and another end adheres to the skin adjacent the other nasal passage. The flexible strip has two resilient bands these being chosen so that they naturally spring apart and drag the skin and therefore the outer wall tissue outwardly to keep the respective passages more open.

An alternative system has a bifurcate arrangement which has respective legs in the respective nostrils and by, again, a natural springing apart, keeps the outer walls of the nose outwardly distended but from an inside of the nasal passageway.

I have found that the existing methods have disadvantages which can be reduced.

One of these is that the flexible strip traversing the bridge of the nose will be implicitly visible and many are concerned by the appearance of this when being worn.

Further, the application of such a device will generally result in a continuous pulling pressure being applied so that the soft flesh of the nose will be under this continuous force. This can result over time in lack of comfort and possibly pain.

SUMMARY OF THE INVENTION

An object of this invention is to provide the public with a useful alternative.

According to one form of this invention there is provided an arrangement for assisting breathing wherein there is a member adhering to the external surface of one side only of a nose, the member extending along a side of the nose in a position so that the member is positioned to have a first part of the member adhering to the skin of the nose adjacent a bony structure located at a back of the nose, and the member has a further part which is closer to an inlet of the nostril of the nose than the first said part and adhering to the skin of the nose adjacent a soft part of the nose, with the member being shaped and otherwise being characterised so as to hold the soft part of the nose outwardly.

In preference the arrangement is further characterised in that there are two said members adhering to a nose with one member on a first one side of the nose of a wearer and the other member on a second opposite side of the nose of a wearer.

In preference as one alternative the nose is the nose of a person.

In preference as a further alternative the nose is the nose of a horse.

In preference as a further alternative again the nose is the nose of a dog.

In preference each member is in the form of a strip with a first sheet of material having an outermost face having thereon a pressure responsive adhesive adapted to maintain a selected shape of the soft tissue.

In preference there is an arrangement for assisting breathing wherein a member has a part at a first end attached by adhesion to skin immediately adjacent bone toward a back of the nose of a user and a part at an opposite end of the member is attached by adhesion to the skin immediately above a portion of the nose toward a front of the nose which is soft flesh adjacent the nostril, and the member is shaped and positioned so as to effect a pulling outwardly of the flesh adjacent the nostril.

In preference the member is comprised of a laminate of a first pliable sheet with an outer surface coated by adhesive shaped and otherwise characterised to be located along a side of a nose, and a second pliable sheet holding a strut between itself and the first sheet.

In a further preferred arrangement there is an arrangement for assisting breathing by being attachable by adhesion along one side of a nose to effect a maintaining of dilation to a nasal passage of the nose characterised in that the member is of elongate shape and is curved so as to have a face defining a convex shape and a contact adhesive being only on the convex side.

In a further preferred arrangement there is an arrangement for assisting breathing by being attachable by adhesion along one side of a nose to effect a dilation force of a nasal passage characterised in that the member is a laminate comprised of a first pliable sheet with an outer surface coated by adhesive, a strut, and a second pliable sheet holding the strut between itself and the first sheet, the member being of elongate shape and is curved so as to have a side following a convex path and a contact adhesive being only on the convex side.

In preference for horses the angle is approximately 30 degrees.

In preference the strut is comprised of aluminium.

BRIEF DESCRIPTION OF THE DRAWING

For a better understanding of this invention it will now be described with reference to preferred embodiments which shall be described with the assistance of drawings wherein:

FIG. 5 is a side perspective view of a horse incorporating the invention according to a second embodiment;

FIG. 6 is a plan view of the element according to the second embodiment; and

FIG. 7 is a side cross sectional view of the second embodiment as shown in preceding FIGS. 5 and 6.

DETAILED DESCRIPTION OF THE PREFERRED EMBODIMENTS

Figure 1:
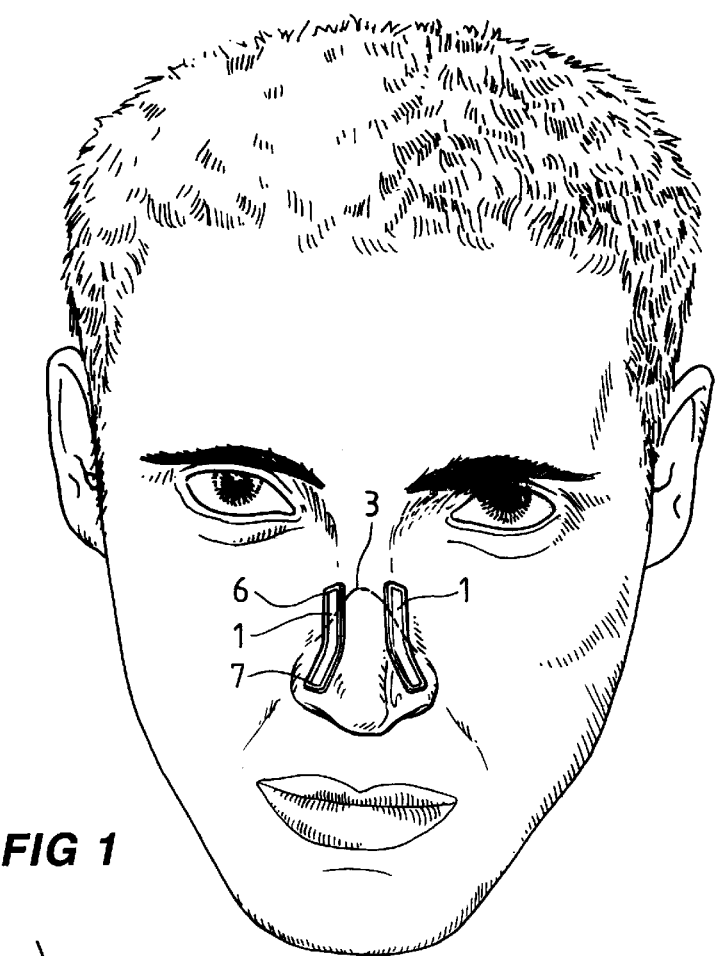
FIG. 1 is a front view of a person with the arrangement according to the first embodiment fitted to both sides of their nose.
Figure 2:
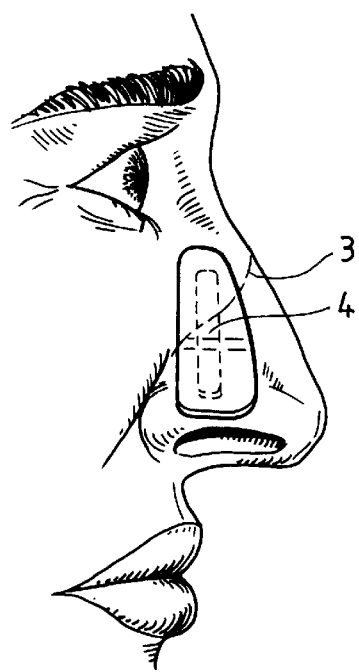
FIG. 2 is a side view of the same embodiment installed in place on the side of the nose.
Figure 3:
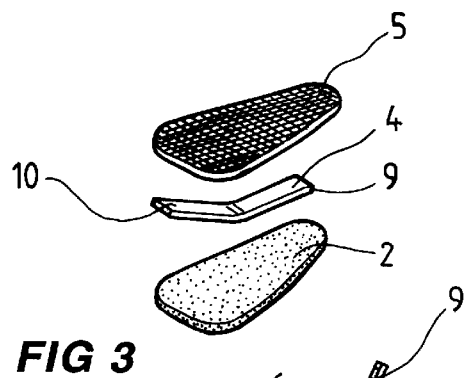
FIG. 3 is an exploded view of the components making up the element of the first embodiment.
Figure 4:
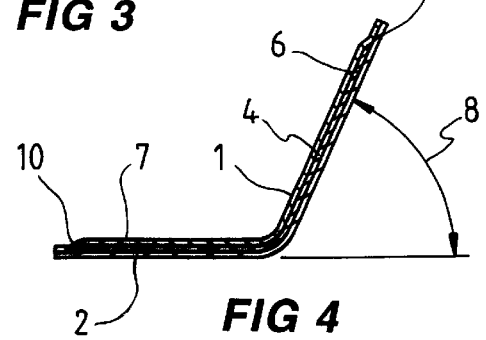
FIG. 4 is a side elevation of the element of the first embodiment.

Now describing the embodiments and referring to the drawings in detail a member 1 in the form of a strip and comprised of a first sheet 2 having on an underneath side an adhesive chosen to enable contact pressure between the adhesive and the skin of a nose to ensure that adhesion will occur with sufficient strength upon an applied pressure between the two surfaces to then enable the member to act to pull or hold relevant skin of the nose and its underlying soft tissue in or into a dilation position.

The structure of a human nose is such that there is a hard part which is bone that starts about half way up or toward a back of the nose which bone is a part of the skull of the person. What is being achieved in accord with this invention is that this hard or bone part which is underlying flesh and skin to which the first end is adhered to which is shown to be further from the nostril of the nose than a dotted line at 3 and is used to support a part at a first end of the strip 1. This portion of the nose is referred to as the rigid fleshy portion. This, as in the manner of a cantilever, can be used to "anchor" the one end of the strip 1 so that it can be used to locate and support in an appropriate position the part of the strip 1 at an opposite end of the strip (which is to say toward the part of a nose further down the face or toward an outer end of the nostril) so as to hold soft tissue of the side of the nose in an outwardly dilated position. The outer or forward portion of the nose is the vestibule, and the ostium internum is located between the vestibule and the rigid fleshy portion. Both the vestibule and the ostium internum comprise the soft fleshy portion of the nose.

This is achieved by having the shape of the member defined by a strut 4 which is a thin strip of aluminium which is sandwiched between the sheet 2 and a top sheet 5 and has a shape that is elongated, and has a part at one end 6 approximately straight, and another part at an opposite end 7 approximately straight and these two parts 6 and 7 at respective opposite ends 9 and 10 are at an angle of approximately 60 degrees (shown at 8) one to the other.

The strut 4 is chosen from aluminium of 0.3 mm thickness and of a grade such that it is pliable and therefore can be changed in shape simply by using finger pressures but not so soft or pliable that when in position of holding a dilation position of the tissue of the nose that it will unduly distort and therefore not achieve sufficiently the result required. This can be readily tested for any user by simple trial and error. Aluminium sheet of this thickness of 0.3 mm as supplied from a manufacturer in Australia has been used satisfactorily both in a hardened state as supplied and also in a softened state by heating the hardened sheet for a period of several hours. Both materials performed adequately showing that a range of grades of materials and quality of materials will be useful.

Other materials can be used but aluminium sheet has been found to be most suitable. One of the characteristics that is useful is the fact that the aluminium apart from being pliable and therefore being able to be shaped by a user for comfort, is also resilient so that when deformed into a position by the user the aluminium can be resiliently deformed further. This can assist in applying further continuing tension adjacent a narrow part of the nasal passage. As a guide to the extent of resiliency that has been found to be useful the strut material in the embodiment having the dimensions of 15 mm×3 mm×0.3 mm if anchored at one end so as to be supported as a cantilever from 1 mm of anchored end then 30 grams will deflect the outer end by 3 mms. These dimensions are also the dimensions of the strut when bent as described that are most appropriate for use by adult humans for the invention. As a guide to the size range of a strut for adult humans the strut can be most usefully within the range of from 12–15 mm in length and 2.5–3.5 mm in width.

One of the advantages of the embodiment is that in use an effect of the strip is to act as a splint so that pressures or more correctly tensions applied will be contributed to by the natural springiness of the flesh to which the strip is attached. This means that, as the act of placing the strip in position means that one will distort the flesh to have this adhere to the relative positions of the parts of the strip, this will mean that the flesh will be held from returning to an original position by the splint effect of the strip. This compares with a strip that bridges the nose which in a commercial production situation needs to be of a size to apply to all manner of sizes and shapes of noses. Accordingly this needs to be able to spring apart substantially and therefore the result is that this will have a tendency to apply constant tension over a substantial range of movement. It is this that over time can become quite uncomfortable.

By having an arrangement that will have a reference position that is immediately adjacent (this is the bone) the position of the applied tension means that this will implicitly provide a predominately position reference as compared to a maintained tension. The result provides more comfort for a user.

The bend in the strut 4 is located just adjacent to where a hard part (the bone) beneath or adjacent the soft tissue of the nose begins. If this is located fully on the hard part of the nose then it is found that soreness can develop after only some few hours of use because there will be a continuous pressure point at the bend.

The material to be used for the sheets 2 and 5 and adhesive both for the outer face of the sheet 2 and the joining between the strut 4 and the sheet 5 is such that it will need to be compatible for use against the skin of humans. Hypoallergenic material is an appropriate material.

In use the element is located so that the bend is just below the hard (that is the bone) part of the nose and on one side of the nose and the soft tissue is then manipulated out by hand usually by the user so as to be adhered to the adhesive outer surface of the sheet 2. The strut can thereafter be changed in shape by finger pressure. The concept however is that this can then hold outwardly the soft tissue adjacent the narrow part of the nasal passage and therefore both resist it being drawn in when greater air volume passes through but also for day to day use for those with deformed nasal passage shapes or those suffering from incidental blockage from rhinitis will also find value in the arrangement.

This concept therefore differs in some important ways from that disclosed in the US Patent in that this concept is found not to be so visually obvious because it does not go across the bridge of the nose. Further it seems to allow for more comfortable use and from experiments conducted so far the results appear to be even more effective in providing nasal clearance. This is believed to be the case because the strip acts more in the manner of a splint and does not need to be designed to allow for continuous outward pressure or more correctly tension but rather simply to allow for holding of the flesh against contracting inwardly or at least against being pulled inwardly by reduced air pressure when air is breathed through the nasal passage.

The elements can be used for one side only of the nose if desired.

Now I refer to FIGS. 5, 6 and 7 which illustrate the application of the invention to a horse. This is an arrangement very similar to that described for the first embodiment in that the element 11 is comprised of three layers where a first is a sheet 12 with an outermost contact adhesive at 13, a middle layer is a strut 14 comprised of 0.3 mm thickness 6 mm width and 90 mm length of aluminium, and the top sheet 15 covers the other two layers. The strut 14 is bent in the middle at 16 to have two ends 17 and 18 that are each approximately straight but which are inclined 30 degrees one to the other as shown at 19.

The shape of the nasal passage of a horse 20 and the location of a hard part (bone) 21 closely behind the open end of the nostril has meant that the concept works very well also for horses. Accordingly, as shown, the element 11 is attached to be in line along the elongate direction of a horses head 22 and is placed in position by opening the nostril passage out to then be held in the position shown with the strut acting in the manner of a splint to hold against retraction of the flesh.

The same arrangement is used for both sides of the horses head. In practise the arrangement gives very good results for these animals and it is believed that accordingly other animals that need to have enhanced performances such as dogs and sometimes camels may also be advantaged.

The results achieved from trials conducted so far have been outstanding. The strips when in place on a human as described have been able to be worn with great comfort over many days without concern. Further, their location has been appropriate to enable substantial disguise of the strips when in place. Perhaps even more exciting has been that the medical results have been substantial so that there have been on controlled tests substantial improvement in breathing efficiencies as compared to the strips when used that bridge the nose.

What is claimed is:

1. A method for resisting the tendency of the vestibule and the ostium internum of the nose of a mammal to draw in during breathing, the method comprising:

forming a nasal dilator of an elongated, generally rigid, deformable strut bent at an angle, the angle being located generally centrally of its ends to form a generally convex shape, with adhesive material on the convex side of the strut;

applying the dilator to one side of the nose with one end on the rigid fleshy portion, the other end on the vestibule and the ostium internum, and the convex apex of the dilator being generally positioned on the rigid fleshy portion and above the vestibule and the ostium internum;

whereby the vestibule and the ostium internum are maintained in the desired position to resist a tendency of the nasal passage to constrict during breathing.

* * * * *